(12) United States Patent
Nishino et al.

(10) Patent No.: US 8,117,803 B2
(45) Date of Patent: Feb. 21, 2012

(54) VESSEL FILLING SYSTEM

(75) Inventors: Yukinobu Nishino, Kanazawa (JP);
Tokuo Nishi, Kanazawa (JP); Yukihiro Yamamoto, Kanazawa (JP)

(73) Assignee: Shibuya Kogyo Co., Ltd., Kanazawa-Shi, Ishikawa (JP)

( * ) Notice: Subject to any disclaimer, the term of this patent is extended or adjusted under 35 U.S.C. 154(b) by 252 days.

(21) Appl. No.: 12/448,634

(22) PCT Filed: Dec. 26, 2007

(86) PCT No.: PCT/JP2007/075010
§ 371 (c)(1),
(2), (4) Date: Jan. 8, 2010

(87) PCT Pub. No.: WO2008/081833
PCT Pub. Date: Jul. 10, 2008

(65) Prior Publication Data
US 2010/0132307 A1    Jun. 3, 2010

(30) Foreign Application Priority Data

Dec. 28, 2006 (JP) .................. 2006-354654

(51) Int. Cl.
*B67C 7/00* (2006.01)
*B65B 55/08* (2006.01)
*B65B 55/24* (2006.01)

(52) U.S. Cl. ............... 53/167; 53/281; 141/85; 141/89; 250/492.3

(58) Field of Classification Search .......... 53/167, 53/281; 141/85, 89, 92; 250/492.3; *B67C 7/00; B65B 55/08, 55/24*
See application file for complete search history.

(56) References Cited

U.S. PATENT DOCUMENTS

| 4,707,334 A | * | 11/1987 | Gerhard | .......................... 53/167 |
| 5,848,515 A | | 12/1998 | Catelli et al. | |
| 5,896,899 A | * | 4/1999 | Schmitz | .......................... 141/85 |

(Continued)

FOREIGN PATENT DOCUMENTS

EP    1 251 085    10/2002

(Continued)

OTHER PUBLICATIONS

International Search Report dated Mar. 25, 2008 (3 pages).

(Continued)

*Primary Examiner* — Stephen F Gerrity
(74) *Attorney, Agent, or Firm* — Flynn, Thiel, Boutell & Tanis, P.C.

(57) ABSTRACT

Atmosphere in a sterilization box 18 is prevented from entering into a filler chamber 44 side, and also, atmosphere on the filler side is prevented from flowing on the sterilization box 18 side. An intermediate chamber 40 is disposed between the sterilization box 18 for performing sterilization by electron beam irradiation to a vessel 2 and the chamber 44 in which a filler 42 is disposed for filling the sterilized vessel 2 with inner content. A pressure in the intermediate chamber 40 is controlled, by a pressure control device, so as to be higher than a pressure in the sterilization box 18 and higher than a pressure in the chamber 44 provided with the filler 42. Since the pressure in the intermediate chamber 40 is highest, atmosphere in the upstream-side sterilization box 18 is prevented from flowing in the filler 42 side and atmosphere in the chamber 44 for the filler 42 is also prevented from flowing in the sterilization box 18 side.

5 Claims, 3 Drawing Sheets

U.S. PATENT DOCUMENTS

| | | | |
|---|---|---|---|
| 6,475,435 B1 * | 11/2002 | Taggart | 53/167 |
| 7,739,859 B2 * | 6/2010 | Colato et al. | 53/167 |
| 2004/0060261 A1 * | 4/2004 | Py | 53/167 |
| 2005/0188651 A1 * | 9/2005 | Clusserath | 53/167 |
| 2006/0075721 A1 * | 4/2006 | Monti | 53/167 |
| 2006/0185321 A1 | 8/2006 | Raynaud | |

FOREIGN PATENT DOCUMENTS

| | | |
|---|---|---|
| EP | 1 251 085 A1 | 10/2002 |
| FR | 2 818 615 | 6/2002 |
| FR | 2 818 615 A1 | 6/2002 |
| FR | 2 882 341 | 8/2006 |
| FR | 2 882 341 A1 | 8/2006 |
| GB | 1 470 990 | 4/1977 |
| JP | 06263120 A * | 9/1994 |
| JP | 10-287310 | 10/1998 |
| JP | 2000214300 A * | 8/2000 |
| JP | 2003-54521 | 2/2003 |
| JP | 2006061558 A * | 3/2006 |
| JP | 2006-206158 | 8/2006 |
| JP | 2006-314407 | 11/2006 |
| WO | WO 2006030790 A1 * | 3/2006 |

OTHER PUBLICATIONS

Written Opinion dated Mar. 25, 2008 (3 pages).
Notification of Transmittal of Int'l Search Report dated Mar. 25, 2008 (4 pages).
European Search Report dated Nov. 20, 2009 (4 pages).

* cited by examiner

[Fig. 1]
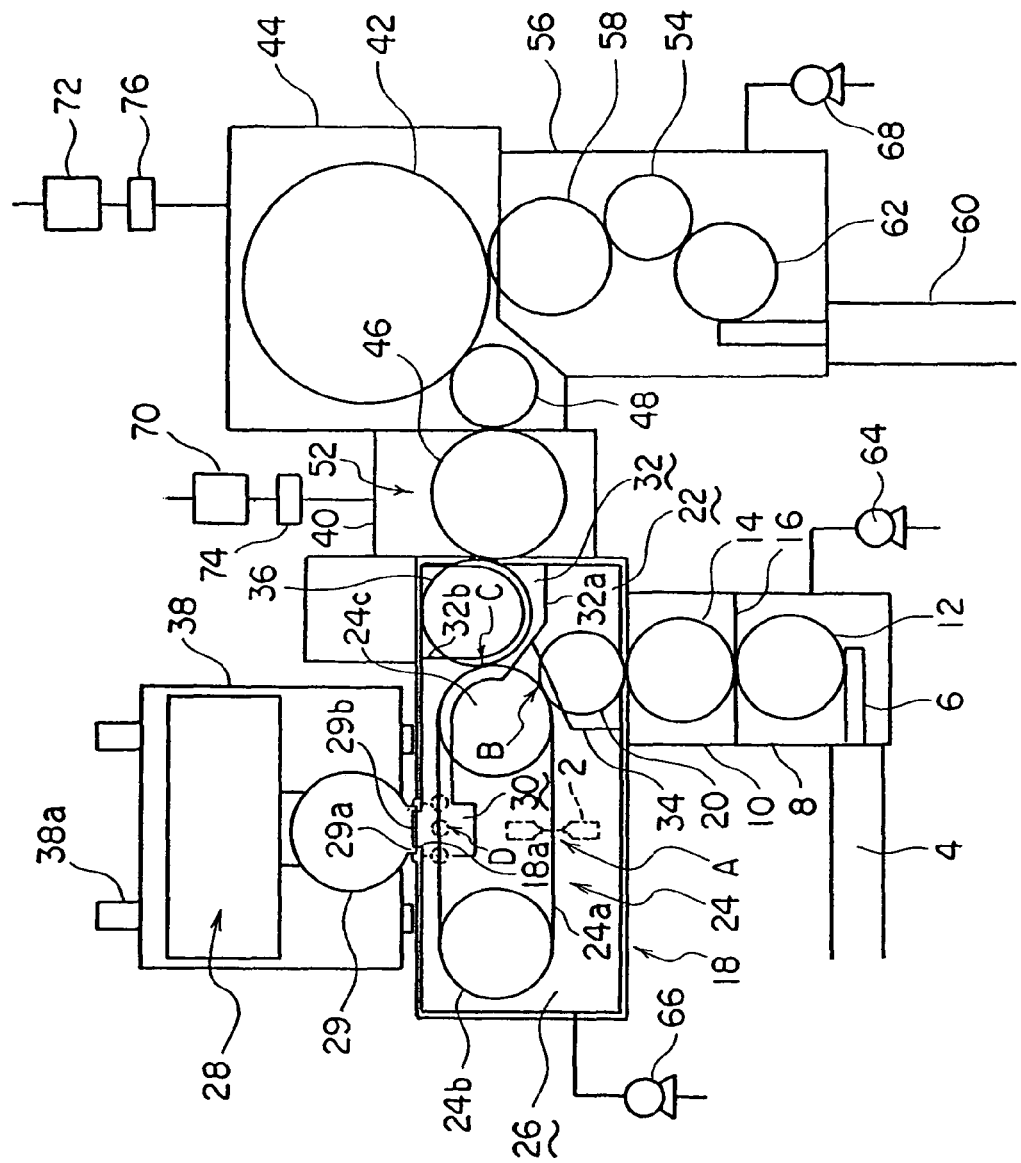

[Fig. 2]
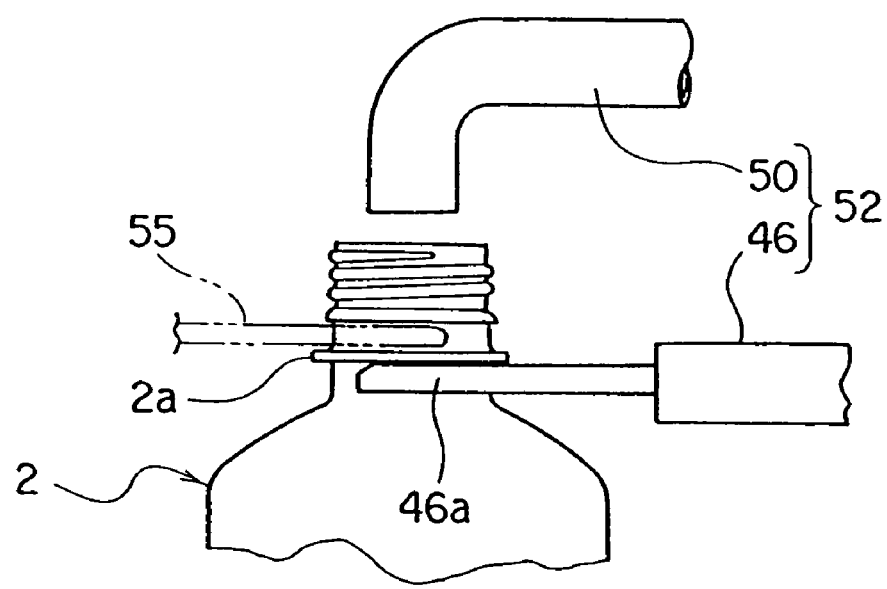

[Fig. 3]
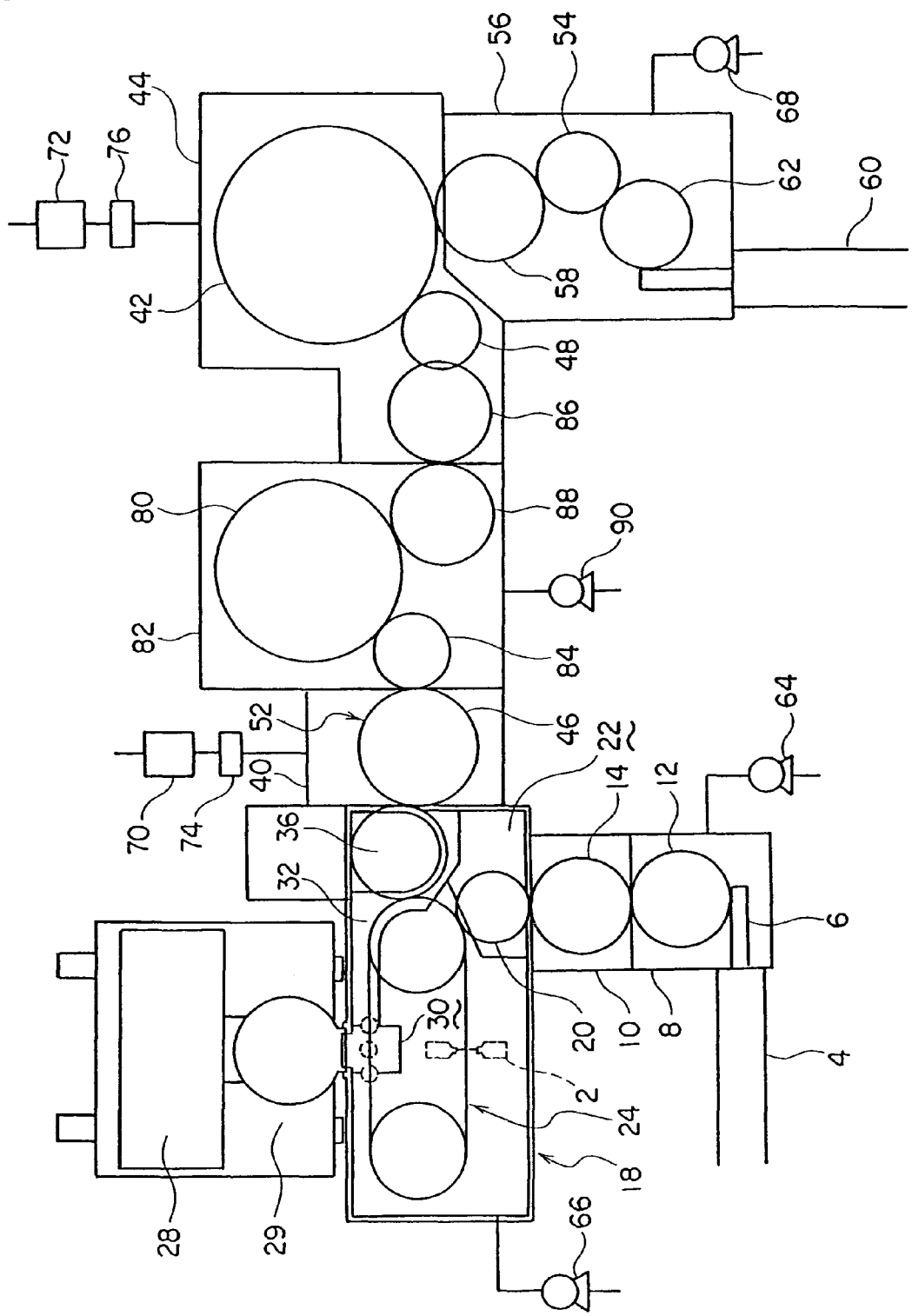

VESSEL FILLING SYSTEM

TECHNICAL FIELD

The present invention relates to a vessel filling system provided with an electron beam irradiation device for sterilizing a vessel by being irradiated with electron beam.

BACKGROUND TECHNOLOGY

There has already been known a vessel filling system for filling a vessel with liquid or like after sterilization of the vessel by the irradiation of electron beam (refer to Japanese Patent Application Laid-open Publication No. 2006-314407). This publication discloses an electron beam irradiation sterilization system provided with an introduction chamber R0, a pre-sterilization chamber R1, a sterilization chamber R2 for performing electron beam sterilization, a rinser chamber R3 blowing air in a vessel, a filling chamber R4 for filling the vessel with inner content, and a capping chamber R5 for applying a cap to a vessel, which are arranged in this order from an upstream side in a vessel conveying direction.

In the sterilization chamber in which the vessel is sterilized by the irradiation of the electron beam, ozone is generated every time the electron beam irradiation. The vessel subjected to the electron beam irradiation is transferred from the sterilization chamber R2 to the rinser chamber R3 with the ozone remaining inside, and when air is blown into the vessel in the rinser chamber R3, the ozone is pushed out of the vessel.

In order to prevent the ozone pushed out of the vessel from flowing into the sterilization chamber R2 arranged upstream side thereof and the filling chamber R4 arranged downstream side thereof, in the invention of the above Patent Publication 1, a pressure P2 in the sterilization chamber R2, a pressure P3 in the rinser chamber R3 and a pressure P4 in the filling chamber R4 are controlled so as to satisfy an relation of P3<P2<P4. That is, the pressure P3 in the intermediately arranged rinser chamber R3 is lowest, the pressure P2 in the sterilization chamber R2 arranged upstream side of the rinser chamber R3 is higher than the pressure P2, and the pressure P4 in the filling chamber R4 arranged downstream side of the rinser chamber R3 is further higher than the pressure P2 in the sterilization chamber R2.

Patent Publication 1: Japanese Patent Application Laid-open Publication No. 2006-314407

DISCLOSURE OF THE INVENTION

Problem to be Solved by the Invention

According to the structure of the above-described Patent Publication 1, the pressure P3 in the intermediately arranged rinser chamber R3 is lower than the pressure P2 in the sterilization chamber R2 arranged upstream side thereof and the pressure P4 in the filling chamber R4 arranged downstream side thereof. However, in the sterilization chamber R2, since a vessel (bottle) conveyed from an outer portion is sterilized, an aseptic state is not maintained. Therefore, even if atmosphere in the sterilization chamber R2 flows into the rinser chamber R3 adjacent to the filling chamber R4 disposed on the downstream side, there is a fear that the external atmosphere may flow into a portion near an entrance of the filling chamber R4. Since it is necessary to maintain the filling chamber R4 to the highest aseptic state (germ free state), even if the pressure P4 in the filling chamber R4 is maintained to the highest pressure, it is not desired that unclean atmosphere approaches the filling chamber R4.

Furthermore, since the pressure P4 in the filling chamber R4 is higher than the pressure P2 in the sterilization chamber R2, there is also a fear that the atmosphere in the filling chamber R4 may flow into the rinser chamber R3 and then into the sterilization chamber R2. Under the electron beam irradiation environment in the sterilization chamber, nitrogen oxide is generated and nitric acid is then generated through the reaction of the generated nitrogen oxide with water. Accordingly, atmosphere including moisture or water content in the filling chamber flows into the sterilization chamber, or in a condition in which a rinsing agent for washing the vessel is provided in the rinser chamber, even if droplets of the rinsing agent in the rinser chamber flows into the sterilization chamber by the air-flow from the filling chamber, nitric acid may generate in the sterilization chamber, which may result in corrosion of an equipment in the sterilization chamber, thus providing a problem.

The present invention was conceived to solve the above problems and an object thereof is to provide a vessel filling system in which pressures in respective chambers are controlled so as to prevent external contaminated atmosphere from entering into a filling chamber side through a sterilization chamber and to prevent water content such as moisture in the filling chamber from entering into the sterilization chamber.

Means for Solving the Problems

The invention is a vessel filling apparatus comprising a sterilization chamber in which a vessel is sterilized by electron beam irradiation, a filling chamber in which filling means for filling the sterilized vessel with inner content is disposed, and pressure control means for controlling pressure conditions between the respective chambers, and characterized in that an intermediate chamber is disposed between the sterilization chamber and the filling chamber, and a pressure in the intermediate chamber is controlled to be higher than a pressure in the sterilization chamber and also to be higher than a pressure in the filling chamber.

The invention is a vessel filling apparatus comprising a sterilization chamber in which a vessel is sterilized by electron beam irradiation, a filling chamber in which filling means for filling the sterilized vessel with inner content is disposed, and pressure control means for controlling pressure conditions between the respective chambers, and characterized in that a cleaning chamber is disposed between the sterilization chamber and the filling chamber for cleaning the vessel sterilized in the sterilization chamber, an intermediate chamber is disposed between the sterilization chamber and the cleaning chamber, and a pressure in the intermediate chamber is controlled to be higher than pressures in the sterilization chamber and the cleaning chamber.

The invention is characterized in that a capper chamber is disposed on a downstream side of the filling chamber and a pressure in the capper chamber is controlled to be lower than that in the filling chamber.

The invention is characterized in that a pressure in a discharge chamber disposed on the most downstream side in the sterilization chamber is controlled to be higher than pressures in an electron beam irradiation chamber and a main chamber both being disposed upstream side of the discharge chamber in the sterilization chamber.

The invention is characterized in that pressures in chambers disposed on an upstream side of the sterilization chamber are controlled to be lower than the pressure in the sterilization chamber and higher than an external pressure.

Effect of the Invention

In the respective inventions mentioned above, the intermediate chamber is disposed between the sterilization chamber and the filling chamber in a condition such that the pressure in the intermediate chamber is higher than that in the sterilization chamber and is equal to or higher than that in the filling chamber, or the intermediate chamber is disposed between the sterilization chamber and the cleaning chamber in a condition such that the pressure in the intermediate chamber is higher than that in the sterilization chamber and higher than that in the cleaning chamber. According to such arrangement, the atmosphere in the sterilization chamber is prevented from entering into the filling chamber and the cleaning chamber, and moreover, the atmosphere containing moisture, water drops and droplets in the filling chamber and the cleaning chamber is also prevented from entering into the sterilization chamber in which the electron beam irradiation is performed.

BRIEF DESCRIPTION OF THE DRAWINGS

FIG. 1 is a plane view showing an entire structure of a vessel filling system provided with an electron beam sterilization apparatus according to a first embodiment of the present invention (Embodiment 1).

FIG. 2 is a front view showing an essential portion of an air-blower.

FIG. 3 is a plane view showing a vessel filling system according to a second embodiment of the present invention (Embodiment 2).

EXPLANATION OF REFERENCE NUMERALS

2 - - - vessel
18 - - - sterilization chamber
42 - - - vessel filling means (filler)
44 - - - filling chamber (chamber for filler)
40 - - - intermediate chamber
56 - - - capping chamber (chamber for capper)
82 - - - cleaning chamber (chamber for rinser)

BEST MODE FOR EMBODYING THE INVENTION

The present invention has a structure including an intermediate chamber disposed between a sterilization chamber in which a vessel is irradiated with electron beam and a filling chamber in which filling means for filling a sterilized vessel with inner content, and pressures in these chambers are controlled by pressure control means such that a pressure in the intermediate chamber is higher than that in the sterilization chamber and is equal to or higher than a pressure in the filling chamber. According to such structure, atmosphere on the filling chamber side is prevented from flowing into the sterilization chamber, and in addition, atmosphere in the sterilization chamber is prevented from flowing in a downstream side through the intermediate chamber, thus achieving the object of the present invention.

Embodiment 1

Hereunder, the present invention will be described with reference to an embodiment shown in the drawings.

In a vessel sterilization apparatus according to this embodiment, a vessel 2 which is filled up with content such as sterilized liquid or like is a PET bottle (see FIG. 2). Such vessels 2 are continuously conveyed by an air conveyer 4, separated from each other at a predetermined interval by an in-feed screw 6, and then, conveyed into an introduction chamber. The introduction chamber is sectioned into two chambers (first introduction chamber 8 and second introduction chamber 10), and rotary wheels (first rotary wheel 12 and second rotary wheel 14) respectively provided with vessel holding means, not shown, are arranged in these chambers 8 and 10.

The vessels 2 conveyed into these introduction chambers 8 and 10 are subsequently transferred to the rotary wheels 12 and 14 in the respective chambers 8 and 10 and then rotated and conveyed. In a wall of the chamber through which the vessel 2 is conveyed from the air conveyer 4 to the first introduction chamber 8, there is formed an opening, not shown, having a size allowing the vessel 2 to pass therethrough, and there is also formed an opening, not shown, through which the vessel 2 is transferred from the first rotary wheel 12 to the second rotary wheel 14, in a partition wall 16 of a vessel transferring portion.

Subsequent to the second introduction chamber 10, there is disposed a sterilization box (sterilization chamber) 18 composed wall sections made of lead to shut off outward leakage of an X-ray (bremsstrahlung) or the electron beam at a time when the vessel 2 is irradiated with the electron beam.

An interior of the sterilization box 18 is divided into an inlet side supply chamber 22 in which a supply wheel 20 is disposed, a main chamber 26 in which a vessel conveying device 24 conveying the vessel 2 received from the supply wheel 20 and turning the vessel upside down, an irradiation chamber 30 which is positioned in front of an electron beam irradiation device 28 and in which the conveying vessel 2 is irradiated with the electron beam, and a discharge chamber 32 which is continuously provided on an outlet side (right side in FIG. 1) of the irradiation chamber 30 and which transfers the vessel 2 sterilized by the electron beam irradiation toward the downstream side while maintaining the aseptic condition.

Furthermore, an opening, not shown, through which the vessel 2 can pass, is formed to a portion of the wall of the sterilization box 18 through which the vessel 2 is transferred from the rotary wheel 14 in the second introduction chamber 10 to the supply wheel 20 in the supply chamber 22. The supply wheel 20 receiving the vessel 2 from the second rotary wheel 14 transfers the vessel 2 to the vessel conveying device 24 in the main chamber 26.

An opening, not shown, allowing the vessel 2 to be transferred therethrough is also formed to a partition wall 34 sectioning the supply chamber 26 and the main chamber 26.

The vessel conveying device 24 disposed in the main chamber 26, though eliminating detailed descriptions of the drawings and the specification, is provided with a vessel holding belt 24a configured as an endless vessel conveyer to which a plurality of vessel grippers as vessel holding means are continuously provided, and two sprockets 24b, 24c, as transfer rotary member, around which the endless vessel holding belt 24a is engaged for circularly conveying the vessel grippers.

The respective vessel grippers are provided with a pair of vertically arranged vessel holding portions to thereby hold and convey two vessels 2, simultaneously, while rotating by 180 degrees around an axis along the conveying direction to thereby take inverted position.

The vessel conveying device 24 includes a straight path for linearly conveying the vessel grippers between both the sprockets 24b and 24c and a circumferential path extending along the respective sprockets 24b and 24c. An inverting position "A" is set to the straight path from one of the sprockets 24c to the other sprocket 24b, so that the vessel 2 is inverted by one turn during the one time circumferential movement of the vessel 2 to change the vertical position of the vessel 2.

On the other hand, in the circumferential path of the one sprocket 24c, a vessel supplying position "B" is set on the downstream side in the vessel gripper conveying direction, and a vessel discharging position "C" is also set on the upstream side thereof. One vessel 2 is held by one of the vessel holding portion at the supplying position "B" and conveyed by two turns in the circumferential direction, during which the vessel 2 is inverted by two turns in its vertical position, and then, after returning to a vessel supplying position, the vessel 2 is transferred to the transfer wheel 36 of the discharge chamber 32 from the discharging position "C". Further, although the first introduction chamber 8, the second introduction chamber 10, the supplying chamber 22 and the main chamber 26 are maintained at a positive pressure state because the vessel 2 before the sterilization is introduced and conveyed therein, the interiors thereof are not maintained in completely aseptic condition.

The electron beam irradiation device 28 is disposed adjacent to the sterilization box 18 made of lead. This electron beam irradiation device 28 is provided with an irradiation unit 29 irradiating the vessel 2 with the electron beam and rested on a mount table 38 to be movable. Structure of this electron beam irradiation device 28 is known, and hence, detailed explanation thereof is not made herein with reference to the drawing and description, but in such device, generally, a filament is heated in a vacuum condition in the irradiation unit 29 to generate thermal electrons, the electrons are then accelerated by high voltage to create thermal high speed electron beams, which are then taken out, into atmosphere, through the window foil 29b such as made of Ti mounted to the irradiation window 29a, and thereafter, the electron beam irradiation is performed to a material (i.e., vessel 2 in this embodiment), thus performing a sterilization process.

In this embodiment, the mount table 38 rested with the electron beam irradiation device 28 is disposed to be movable on a rail 38a so as to approach or separate from the sterilization box 18. When the vessel filling system is operated, the mount table 38 is moved so as to approach the sterilization box 18, the irradiation window 29a of the irradiation unit 29 is made accord with the opening 18a formed to the wall of the sterilization box 18, and then, the sterilization box 18 and the irradiation unit 29 are coupled together.

The irradiation chamber 30 is disposed inside the sterilization box 18 so as to surround the opening 18a to which the irradiation unit 29 is fitted. The straight path extends from the sprocket 24b to the sprocket 24c of the vessel conveying device 24 so as to penetrate the irradiation chamber 30, and an irradiating position "D" is set to a penetrating portion of the straight path. Two vessels 2 held by the vessel grippers pass through the irradiation chamber 30 in a vertically perpendicular attitude, and each of the vessels 2 is sterilized by the irradiation of the electron beam from the electron beam irradiation device 28.

To the wall, on the inlet side and outlet side, of the irradiation chamber 30, there are formed openings, not shown, having sizes allowing the two vessels 2 held vertically in attitude by the vessel grippers to pass therethrough. The discharge chamber 32 is formed to be continuous to the wall of the irradiation chamber 30 on the outlet side thereof. One of the sprockets (right side one 24c in FIG. 1) of the vessel conveying device 24 is disposed in a state intruded into the discharge chamber 32.

The vessel 2 held by the vessel gripper and subjected twice, at vertically upper and lower positions, to the electron beam irradiation is transferred to the transfer wheel 36 disposed in the discharge chamber 32 from the lower vessel holding portion of the vessel gripper.

The discharge chamber 32 includes a conveying path on the side of the vessel conveying device 24 from the outlet opening of the irradiation chamber 30 to the transfer wheel 36 and a conveying path on the side of transfer wheel 36 without disturbing the rotation of the sprocket 24c, and these conveying paths are surrounded by and covered with the partition wall 32a sectioning the space from the main chamber 26 and the supply chamber 22, the partition wall 32b opposing to the partition wall 32a and sectioning from the upper and lower spaces of the transfer wheel 36 and the bottom surface and the ceiling surface of the sterilization box 18. The vessel 2 which has been sterilized by the irradiation of the electron beam is transferred to the following respective chambers continuous to this discharge chamber 32 to be deal with therethrough, so that these chambers are maintained in an aseptic condition.

Further, it may be possible to provide a partition wall which partitions the conveying path on the side of the vessel conveying device 24 from the outlet opening of the irradiation chamber 30 to the transfer wheel 36 into an upper conveying space and lower conveying space without disturbing the conveyance of the vessel 2. It may be also possible to provide a partition wall which partitions the conveying path on the side of the transfer wheel 36 into a lower conveying space in which the vessel 2 is transferred thereto and an upper conveying space so as to be communicated with each other. In this modified arrangement, the discharge chamber 32 may be formed from a space surrounding the lower conveying space and the conveying path of the transfer wheel 36.

An intermediate chamber 40 is disposed adjacent to the discharge chamber 32 positioned on the most downstream side in the sterilization box 18, and a chamber (filling chamber) 44, in which a filler (filling means) 42 is housed, is provided on the downstream side of this intermediate chamber 40. A rotary wheel (neck wheel) 46 provided with vessel holding means 46a (FIG. 2) is disposed inside the intermediate chamber 40, and the neck wheel 46 is operated so as to transfer the vessel 2, received from the transfer wheel 36 in the discharge chamber 32 and then rotated and conveyed, to a supply wheel 48 in the chamber 44 in which the filler 42 is disposed.

Air injection nozzles 50 are arranged, as shown in FIG. 2, above the vessel holding means 46a, respectively, at equal interval in the circumferential direction of the neck wheel 46 disposed in the intermediate chamber 40. The neck wheel 46, the vessel holding means 46a and the air injection nozzles 50 constitutes an air blower device 52. The air blower device 52 serves to blow aseptic air into the vessel 2 from the air injection nozzle 50 during a time when the vessel 2 is rotated and conveyed in a state in which a lower side of a flanged portion 2a formed to the neck portion of the vessel 2 is supported by the vessel holding means 46a.

As mentioned above, by blowing the aseptic air into the vessel 2 which has been sterilized by the irradiation of the electron beam from the electron beam irradiation device 28, ozone generated by the irradiation of the electron beam is discharged outward from the vessel 2.

Further, grippers 55 (shown with virtual line in FIG. 2) gripping the upper portion of the flanged portion 2a of the vessel are provided, respectively, for the transfer wheel 36 transferring the vessel 2 to the neck wheel 46 and the downstream side supply wheel 48 receiving the vessel 2 from the neck wheel 46.

The vessel 2 after being subjected to the air blowing by the air blower device 52 is transferred to the supply wheel 48 disposed on the inlet side in the chamber 44 and then supplied to the filler 42 disposed in the chamber 44. The filler 42 receiving the vessel 2 from the supply wheel 48 fills the vessel 2 with inner content such as liquid during the rotating and conveying operations of the vessel 2 in the held state.

After the completion of the filling, the vessel 2 is conveyed into a chamber (capper chamber) 56 for a capper 54 disposed adjacent to the chamber 44 with the filler 42. An intermediate wheel 58 for receiving the vessel 2 from the filler 42 and transferring the vessel 2 to the capper 54 is disposed on the inlet side of the capper chamber 56.

Further, on the downstream side of the capper 54, a discharge wheel 62 for transferring the vessel 2 after being capped to a discharge conveyer 60.

In the vessel filling system of the structure mentioned above, the vessel 2 conveyed by the air conveyer 4 is sterilized in the sterilization box 18 by being irradiated with the electron beam from the electron beam irradiation device 28, then filled up with the inner content by the filler 42, capped by the capper 54, and thereafter, discharged by the discharge conveyer 60 so as to be subjected to the following procedure.

Further, openings through which the vessel can pass are formed respectively to the wall portions at a position at which the vessel 2 is transferred from the transfer wheel disposed in the discharge chamber 32 in the sterilization box 18 to the rotary wheel 46 to the intermediate chamber 40, at a position at which the vessel 2 is transferred from the rotary wheel 46 in the intermediate chamber 40 to the supply wheel 48 in the chamber 44 in which the filler 42 is disposed, and at a position at which the vessel 2 is transferred from the filler 42 to the intermediate wheel 58 disposed in the chamber 56 in which the capper 54 is disposed.

Furthermore, shutters are provided for the respective openings formed to the sterilization box 18 so as to close the openings at a time of cleaning the chambers communicated with the inside of the sterilization box 18 to thereby prevent water drops or moisture from entering thereinto.

Air exhaust blowers 64, 66 and 68 are connected respectively to the first introduction chamber 8, the main chamber 26 of the lead sterilization box 18 and the chamber 56 in which the capper 54 is disposed so as to exhaust air in the respective chambers 8, 26 and 56. Further, pressurized air supply means 70 and 72 are connected respectively to the intermediate chamber 40 in which the air blower device 52 and the chamber 44, in which the filler 42 is disposed, through filters 74 and 76, respectively so as to supply the aseptic air into the respective chambers 40 and 44.

The respective exhaust blowers 64, 66 and 68, the pressurized air supply means 70 and 72, and a control device, not shown, controlling the air exhaust amount and air supply amount constitute a pressure control means, by which the pressures in the respective chambers 8, 10, 22, 26, 32 40, 44 and 56 are controlled.

In this embodiment, the inside of the intermediate chamber 40 disposed between the sterilization box 18 including the electron beam irradiation chamber 30 in which the sterilization of the vessel 2 is subjected to the electron beam irradiation and the chamber 44 in which the filler 42 is disposed, is controlled so as to provide the highest pressure. Moreover, a pressure in the inside of the chamber 44 in which the filler 42 is disposed is controlled to be equal to or slightly lower than the pressure in the intermediate chamber 40.

Further, the inside of the chamber 56, in which the capper 54 is disposed, disposed on the downstream side of the chamber 44 in which the filler 42 is disposed, is controlled so as to provide a pressure lower than the pressure in the chamber 44. On the other hand, a pressure in the inside of the discharge chamber 32 in the sterilization box 18 disposed on the upstream side of the intermediate chamber 40 is controlled so as to provide a pressure lower than the pressure in intermediate chamber 40, and pressures in the irradiation chamber 30 and the main chamber 26 are lower than that in the discharge chamber 32.

Furthermore, pressures in the insides of the supply chamber 22, the second introduction chamber 10 and the first introduction chamber 8, which are disposed on the upstream side of the main chamber 26, provide positive pressures more than that of the outside, but these pressures are controlled so as to become gradually lower toward the upstream side thereof.

Furthermore, although the sterilization chamber recited in patent claims 1 and 2 is denoted as the sterilization chamber 18, the inside of the intermediate chamber 40 is controlled so as to provide a pressure higher than the pressure in the downstream-side discharge chamber 32 the inside of which is maintained so as to provide the highest pressure in the sterilization box 18.

An operation of the vessel filling system of the structures mentioned above will be explained hereunder.

The vessel 2, which is sterilized and filled up with inner content by this vessel filling system, is a PET bottle, and the PET bottle 2 is held by holding the lower side of the flanged portion 2a formed to the neck portion thereof and conveyed by the air conveyer 4 by blowing the air from the rear side of the PET bottle 2. The vessels 2 conveyed by the air conveyer 4 enter into the first introduction chamber 8, in which the vessels 2 are separated at a constant interval and then transferred to the vessel holding means of the first rotary wheel 12. Further, the vessels 2 are rotated and conveyed by the first rotary wheel 12, and then, transferred to the second rotary wheel 14 disposed in the second introduction chamber 10.

Each of the vessels 2 is then transferred to the supply wheel 20 disposed inside the supply chamber 22 of the lead sterilization chamber 18 from the second rotary wheel 14, and rotated, conveyed and then transferred to the gripper of the vessel conveying device 24 in a state held by the vessel holding means of the supply wheel 20. The gripper has upper and lower two vessel holding portions, and the vessel 2 held by the lower vessel holding portion moves upward and turns upside down by inversely turning the gripper to thereby take an inverted state. The inverted vessel gripper is moved so as to turn around the periphery of the sprocket 24b and enters into the irradiation chamber 30. In the irradiation chamber 30, the vessel 2 is subjected to the irradiation with the electron beam generated by the electron beam irradiation device 28 disposed outside the irradiation chamber 30. The conveyed vessel 2 is irradiated with the electron beam and sterilized during the passing forward the irradiation surface (window foil 29b) of the irradiation unit 29.

The vessel 2 subjected to the first irradiation with the electron beam passes throughout the irradiation chamber 30, moves inside the discharge chamber 32, turns around the periphery of the sprocket 24c and then returns to the vessel supply position "B" at which the vessel 2 was supplied from the supply wheel 20. The vessel 2 which was received by the lower side vessel holding portion in the preceding operation, mentioned above, has been turned to an upper position, and hence, the other vessel holding portion disposed on the lower side receives this time the vessel 2 from the supply wheel 20.

Thereafter, the gripper is again turned upside down so that the vessel subjected to the irradiation of the electron beam at the upper position is moved to the lower side, and in this state, the surface which is not irradiated with the electron beam faces the outer side in the rotating direction of the vessel conveying device 24.

When the vessel 2 again enters into the irradiation chamber 30, the vessel 2 subjected to the first electron beam irradiation is subjected to the second electron beam irradiation from the side opposite to the first electron beam irradiation side, thus the entire inside and outside surface areas of the vessel being sterilized. Simultaneously, the vessel 2 positioned on the upper side and held by the other vessel holding portion is subjected to the first electron beam irradiation.

The vessel 2 of which entire inside and outside surfaces are sterilized by the second electron beam irradiation in the electron beam irradiation chamber 30 is transferred to the transfer wheel 36 in the discharge chamber 32, then transferred to the neck wheel 46 in the intermediate chamber 40 and discharged thereafter from the lead sterilization box 18. During the rotating and conveying of the vessel, the aseptic air is injected, from the air injection nozzle 50 disposed upside, inside the vessel 2 held by the vessel holding means 46a of the neck wheel 46 disposed in the intermediate chamber 40, and thereby, the ozone generated by the irradiation with the electron beam and remaining inside the vessel 2 is exhausted.

The vessel 2 held by the neck wheel 46 of the intermediate chamber 40 is thereafter transferred to the supply wheel 48 disposed inside the chamber 44 in which the filler 42 is disposed. Thereafter, the vessel 2 is supplied to the filler 42 from the supply wheel 48. The vessel 2 filled up with the inner content by the filler 42 during the rotation and conveyance is taken out from the filler 42 by the intermediate wheel 58 and then conveyed into the chamber 56 in which the capper 54 is disposed. The vessel 2 conveyed inside the chamber 56 is transferred to the capper 54 from the intermediate wheel 58 and subjected to the capping operation, and thereafter, the vessel is discharged on the discharge conveyer 60 through the discharge wheel 62 to be subjected to the next process.

In the vessel filling system according to this embodiment, a pressure in the intermediate chamber 40 disposed between the discharge chamber 32 adjacent to the intermediate chamber 40 in the sterilization box 18 made of lead and the chamber 44 in which the filler 42 is disposed is controlled so as to be maintained to the highest pressure by the pressure control means. Therefore, atmosphere in the sterilization box 18 into which the vessel 2 is conveyed from the outside is blocked by the pressure in the intermediate chamber 40 and prevented from entering into the intermediate chamber 40, and moreover, it is also prevented from entering into or approaching the chamber 44, in which the filler is disposed, disposed further downstream side of the intermediate chamber 40. Furthermore, atmosphere including moisture in the chamber 44 provided with the filler 42 is blocked by the pressure in the intermediate chamber 40 and then prevented from entering into the intermediate chamber 40, and hence, prevented from entering into the sterilization box 18, in which the electron beam irradiation is performed, disposed further upstream side of the intermediate chamber 40.

Second Embodiment 2

FIG. 3 is a plane view representing an entire structure of a vessel filling system according to the second embodiment of the present invention. Further, since the basic structure of this embodiment is substantially the same as that of the first embodiment, the same reference numerals are added to corresponding members or like and duplicated explanation will be omitted hereunder, and only the different portions are explained.

In the vessel filling system of this embodiment, a chamber (cleaning chamber) 82 provided with a rinser (cleaning means) 80 is disposed between the intermediate chamber 40 and the chamber (filling chamber) 44 in which the filler 42 is disposed. In the chamber 82 for the rinser 80, there are disposed: a supply wheel 84 for supplying the vessel 2 within the rinser 80 from the neck wheel 46 in the intermediate chamber 40; and a discharge wheel 88 for taking out the vessel 2 cleaned in the rinser 80 and transferring the same to a transfer wheel 86 disposed in the chamber 44 provided with the filler 42.

Furthermore, a discharge blower 90 is connected to the chamber 82 for the rinser 80, and this discharge blower 90, the exhaust blowers 64, 66, 68, the air supply means 70, 72, having structures similar to those of the first embodiment, and a control device, not shown, construct pressure control means. Further, inside the intermediate chamber 40 of this embodiment, an air jetting nozzle constituting the air-blower device 52 in the first embodiment is not disposed.

In this embodiment, the inside of the intermediate chamber 40 provides the highest pressure, and a pressure in the upstream-side sterilization box 18 (especially, a pressure in the discharge chamber 32 adjacent to the intermediate chamber 40) is lower than the pressure in the intermediate chamber 40.

Furthermore, the pressures in the main chamber 26, the supply chamber 22, the second introduction chamber 10 and the first introduction chamber 8, all being disposed on the upstream side of the discharge chamber 32, provide positive pressures more than the outside pressure as like in the first embodiment, but these pressures are gradually reduced toward the upstream side.

On the other hand, on the downstream side of the intermediate chamber 40, the pressure in the chamber 82 in which the rinser 80 is disposed is a positive pressure more than that of the outside thereof but is lower than the pressure in the intermediate chamber 40, and also lower than that in the chamber 44 for the filler 42.

In this second embodiment, atmosphere on the sterilization box 18 side into which the vessel 2 is conveyed from the external side is blocked by the pressure in the intermediate chamber 40 and prevented from entering into the respective chambers disposed downstream side thereof. Furthermore, droplet or water drop from the rinser 80 and atmosphere containing moisture in the chamber 82 provided with the rinser 80 and the chamber 44 are blocked by the pressure in the intermediate chamber 40 and prevented from entering into the sterilization box 18, disposed upstream side thereof, in which the electron beam irradiation is carried out.

Moreover, the rinser 80 is constructed so as to jet aseptic water onto the inner and outer surfaces of the vessel to clean the surfaces for the purpose of removing adhering material such as dust or dirt and foreign material in the vessel 2 at the time when the vessel 2 sterilized by the electron beam irradiation is conveyed into the filling chamber. However, as cleaning means such as rinser disposed in the chamber (cleaning chamber) 82, air-rinser or air-cleaner may be utilized for removing the dust or dirt and foreign material by blowing the aseptic air onto the inner and outer surfaces of the vessel 2, or reversing the vessel 2 or sucking the interior thereof.

The invention claimed is:

1. A vessel filling apparatus comprising a sterilization chamber (18) in which a vessel (2) is sterilized by electron beam irradiation, a filling chamber (44) in which filling means (42) for filling the sterilized vessel (2) with inner content is disposed, and pressure control means for controlling pressure conditions between the respective chambers, wherein an intermediate chamber (40) is disposed between the sterilization chamber (18) and the filling chamber (44), and a pressure in the intermediate chamber (40) is controlled to be higher than a pressure in the sterilization chamber (18) and also to be higher than a pressure in the filling chamber (44).

2. A vessel filling apparatus comprising a sterilization chamber (18) in which a vessel (2) is sterilized by electron beam irradiation, a filling chamber (44) in which filling means for filling the sterilized vessel (2) with inner content is disposed, and pressure control means for controlling pressure conditions between the respective chambers, wherein a cleaning chamber (82) is disposed between the sterilization chamber (18) and the filling chamber (44) for cleaning the vessel (2) sterilized in the sterilization chamber (18), an intermediate chamber (40) is disposed between the sterilization chamber (18) and the cleaning chamber (82), and a pressure in the intermediate chamber (40) is controlled to be higher than pressures in the sterilization chamber (18) and the cleaning chamber (82).

3. The vessel filling apparatus according to claim 1, wherein a capper chamber (56) is disposed on a downstream side of the filling chamber (42) and a pressure in the capper chamber (56) is controlled to be lower than that in the filling chamber (42).

4. The vessel filling apparatus according to claim 1, wherein a pressure in a discharge chamber (32) disposed on a most downstream side in the sterilization chamber (18) is controlled to be higher than pressures in an electron beam irradiation chamber (30) and a main chamber (26), both being disposed on an upstream side of the discharge chamber (32) in the sterilization chamber (18).

5. The vessel filling apparatus according to claim 1, wherein pressures in chambers (8, 10) disposed on an upstream side of the sterilization chamber (18) are controlled to be lower than the pressure in the sterilization chamber (18) and higher than an external pressure.

* * * * *